(12) United States Patent
Noca et al.

(10) Patent No.: US 7,175,762 B1
(45) Date of Patent: Feb. 13, 2007

(54) NANOCARPETS FOR TRAPPING PARTICULATES, BACTERIA AND SPORES

(75) Inventors: Flavio Noca, Altadena, CA (US); Brian D. Hunt, La Crescenta, CA (US); Michael J. Bronikowski, Altadena, CA (US); Michael E. Hoenk, Valencia, CA (US); Robert S. Kowalczyk, Santa Clarita, CA (US); Daniel S. Choi, Los Angeles, CA (US); Fei Chen, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 25 days.

(21) Appl. No.: 10/455,873

(22) Filed: Jun. 6, 2003

Related U.S. Application Data

(60) Provisional application No. 60/386,526, filed on Jun. 6, 2002.

(51) Int. Cl.
*B01D 46/50* (2006.01)
*B01D 63/00* (2006.01)
*B01D 57/02* (2006.01)

(52) U.S. Cl. .......................... 210/500.22; 210/321.75; 210/321.84; 210/488; 210/503; 204/450; 204/600; 977/720; 977/742; 977/746; 977/725

(58) Field of Classification Search .......... 210/500.22, 210/321.75, 321.84, 488, 503; 204/450, 204/600; 977/DIG. 1
See application file for complete search history.

(56) References Cited

U.S. PATENT DOCUMENTS

| | | | |
|---|---|---|---|
| 5,443,955 A | 8/1995 | Cornell et al. | |
| 5,837,115 A * | 11/1998 | Austin et al. | 204/450 |
| 6,027,623 A | 2/2000 | Ohkawa | |
| 6,232,706 B1 | 5/2001 | Dai et al. | |
| 6,278,231 B1 * | 8/2001 | Iwasaki et al. | 313/310 |
| 6,628,053 B1 * | 9/2003 | Den et al. | 313/310 |
| 6,685,810 B2 * | 2/2004 | Noca et al. | 204/450 |
| 6,756,795 B2 * | 6/2004 | Hunt et al. | 324/701 |
| 2001/0024633 A1 * | 9/2001 | Lee et al. | 423/447.3 |
| 2003/0052006 A1 | 3/2003 | Noca et al. | |
| 2003/0165418 A1 * | 9/2003 | Ajayan et al. | 423/447.2 |
| 2003/0185985 A1 * | 10/2003 | Bronikowski et al. | 427/258 |
| 2004/0149209 A1 * | 8/2004 | Dai et al. | 118/715 |

OTHER PUBLICATIONS

Baughman et al, "Carbon Nanotube Actuators", Science 284 1340 (1999).*
International Search Report from International Application No. PCT/US2003/017912 filed Jun. 6, 2003 (7 pgs).
Written Opinion from International Application No. PCT/US2003/017912 filed Jun. 6, 2003 (5 pgs).
Heuberger et sl., "Density Fluctuations Under Confinement: When Is a Fluid Not a Fluid? ", Science, May 4, 2001, vol. 292, pp. 905-908.

(Continued)

*Primary Examiner*—Krishnan S. Menon
(74) *Attorney, Agent, or Firm*—Christie, Parker & Hale, LLP

(57) ABSTRACT

A nanofeature particulate trap comprising a plurality of densely packed nanofeatures, such as nanotubes, and a particulate detector incorporating the nanofeature particulate trap are provided. A method of producing a nanotrap structure alone or integrated with a particulate detector is also provided.

18 Claims, 9 Drawing Sheets

OTHER PUBLICATIONS

Israelachvili, "Chapter 6, Van der Waals Forces", Intermolecular and Surface Forces, Academic Press, date unknown, pp. 83-108, cover page.

Israelachvili, "Chapter 11, Van der Waals Forces Between Surfaces", Intermolecular and Surface Forces, Academic Press, date unknown, pp. 176-212, cover page.

Autumn et al., "Adhesive Force of a Single Gecko Foot-Hair", Nature, Jun. 8, 2000, vol. 405, pp. 681-685.

Baughman et al., "Carbon Nanotube Actuators", Science, May 21, 1999, vol. 284, pp. 1340-1344.

Murakami et al., "Field Emission From Well-Aligned, Patterned, Carbon Nanotube Emitters", Applied Physics Letters, Mar. 27, 2000, vol. 76, No. 13, pp. 1776-1778.

Li et al., "Carbon Nanotube Films Prepared by Thermal Chemical Vapor Deposition at Low Temperature for Field Emission Applications", Applied Physics Letters, Sep. 10, 2001, vol. 79, No. 11, pp. 1670-1672.

Choi et al., "Growth of Carbon Nanotubes by Microwave Plasma-Enhanced Chemical Vapor Deposition at Low Temperature", J. Vac. Sci. Technol. A, Jul./Aug. 2000, vol. 18, No. 4, pp. 1864-1868.

Lee et al., "Low-Temperature Growth of Carbon Nanotubes by Thermal Chemical Vapor Deposition Using Pd, Cr, and Pt as Co-Catalyst", Chemical Physics Letters, Sep. 15, 2000, vol. 327, pp. 277-283.

Zhang et al., "Formation of Single-Wall Carbon Nanotubes by Laser Ablation of Fullerenes at Low Temperature", Applied Physics Letters, Nov. 15, 1999, vol. 75, No. 20, pp. 3087-3089.

Chen et al., "Plasma-Induced Low-Temperature Growth of Graphitic Nanofibers on Nickel Substrates", Journal of Crystal Growth, 1998, vol. 193, pp. 342-346.

* cited by examiner

NANOCARPETS FOR TRAPPING PARTICULATES, BACTERIA AND SPORES

CROSS-REFERENCE TO RELATED APPLICATION

This application is based on and claims priority to U.S. Provisional Application No. 60/386,526, filed Jun. 6, 2002.

STATEMENT REGARDING FEDERALLY SPONSORED RESEARCH

The U.S. Government has certain rights in this invention pursuant to grant No. NAS 7-1407, awarded by the National Aeronautics and Space Administration, Office of Space Science.

FIELD OF THE INVENTION

The present invention is directed to the growth of dense mats or carpets of nanotubes, and more particularly to the growth of dense carpets of carbon nanotubes for use in trapping small particles for in-situ detection.

BACKGROUND OF THE INVENTION

Nanoscale structures are becoming increasingly important because they provide the basis for devices with dramatically reduced power and mass, while simultaneously having enhanced capabilities, and previous patent applications have disclosed the advantageous use of such nanostructures in a number of different real-time, molecule specific sensors.

However, very often airborne and waterborne microbiological entities, such as macro-biomolecules, spores, bacteria, etc. occur in such low concentrations that real-time detectors are ineffective at sensing them. In addition, the identification of these particulates often requires some form of intrusive analysis (tagging, DNA extraction, etc.), which cannot be accomplished if the particulate is free to move away from the location of the detector. Finally, while many of the current nano-sensors are very sensitively tuned to capture and identify one particular species (DNA strands, *Salmonella* etc.), the devices may miss all the other particulates of interest present in the environment.

To solve these problems a system is needed to trap all molecules of interest for later analysis by a more conventional detection means. One conventional method of filtering, or trapping small particles is to use high surface area charcoal. Indeed, the ancient Egyptians understood the beneficial properties of charcoal as a filter, which was used to improve the quality of drinking water.

The modern successor of charcoal is activated carbon. Activated carbon is a carbonaceous adsorbent with high internal porosity, and hence a large internal surface area of 500 up to 1500 m^2/g. Activated carbon mainly consists of elementary carbon in a graphite-like structure. It can be produced by heat treatment, or "activation", of raw materials such as wood, coal, peat and coconuts. During the activation process, the unique internal pore structure is created, and it is this pore structure which provides activated carbon its outstanding adsorptive properties. Activated carbon finds uses in a myriad of applications, from adsorption or chemisorption, to removal of chlorine through reduction reactions, as a carrier of catalytic agents, as a support material for biofilters, or as a chemical carrier for the slow release of coloring agents.

For example, since 1991, activated carbon adsorption has been widely adopted for dioxin removal from waste incinerators in Europe and Japan. Because of the higher bond energy between dioxin and activated carbon than other sorbents, the removal efficiency for dioxin by activated carbon is much higher than other sorbents, including clays, pillared clays, gamma-alumina, and zeolites.

However, although high surface area activated charcoal is an excellent trapping material, the three-dimensional nature of the high surface area matrix makes it very difficult to use standard detection schemes, laser diagnostics techniques (UV fluorescence and other non-linear light scattering techniques) to actually distinguish the particles of interest (such as those containing proteins, nucleic acids, and coenzymes) from other organic and inorganic particulate contaminants.

Accordingly, a need exists for improved nanoscale material for use as a trapping material for concentrating low concentrations of airborne and waterborne particles for detection by highly sensitive, robust, and cost-effective in situ sensors.

SUMMARY OF THE INVENTION

The present invention is directed to a nanofeature particulate trap comprising a plurality of densely packed nanofeatures, such as nanotubes. The invention is also directed to a particulate detector incorporating the nanofeature particulate trap.

In one embodiment, the nanofeature particulate trap is substantially two-dimensional.

In another embodiment, the nanofeatures are hydrophobic. In such an embodiment the nanofeature trap may be particularly suited for liquid environments.

In still another embodiment, the nanofeatures are chosen to have a large surface-to volume ratio such that surface interactions are promoted.

In yet another embodiment, the radius of curvature of the nanofeatures is confined to provide a nanofeature trap having large Van der Waals forces.

In still yet another embodiment, the nanofeature trap is in communication with a voltage source such that an electrical field can be generated in the individual nanofeatures of the nanofeature trap. In one such embodiment, the individual nanofeatures may be designed to serve as electron emitting/receiving elements. In an alternative embodiment the application of an electrical field to the nanofeatures is designed to trigger an electromechanical actuation of the individual nanofeatures. In one such embodiment, the nanotrap actuator comprises a nanotrap with an integrated electrode substrate. The nanoscale actuators of the present invention are designed to provide the capability of controllable motion on near-atomic scales. In such an embodiment, the transduction mechanism is symmetric—length changes in the nanotubes will induce charge transfer and hence voltages.

In still yet another embodiment, the nanofeature trap is designed to trap particles as small as 0.5 micron.

This invention is also directed to an analyzer, which utilizes a nanofeature trap in combination with a detector that functions as a molecular sensor. This invention is also directed to novel systems and methods for utilizing nanofeature traps comprising a plurality of densely packed nanotubes with integrated detectors to form a particulate analyzer.

In another embodiment, the invention is directed to a system for the detection of substances comprising multiple nanofeature traps as described above, such that parallel processing of molecules can be carried out.

This invention is also directed to growth and processing techniques to control the physical properties of the individual nanotubes and the density of the trap generally; and methods for positioning the nanotube trap during growth, including nanoscale patterning of the substrate to ensure that the growth of the nanotube trap is located and aligned with any external analysis devices.

In another embodiment the nanotubes comprising the nanofeature trap are self-assembled to have a specified diameter, a specified height, and a specified degree of curling suitable for use in the devices of the current invention.

In still another embodiment, the substrate for the trap is made of a semiconductor such as, for example, oxidized silicon or aluminum oxide, coated with a metal catalyst film such as, for example, Ni or Co. In this embodiment, the silicon can be further doped to adjust the electronic properties of the substrate surface.

In yet another embodiment, the nanotubes comprising the nanofeature trap are self-assembled from an inert material such as, for example, carbon utilizing a carbon feedstock gas such as, for example, ethylene.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The present invention is directed to a nanofeature particulate trap comprising a plurality of densely packed nanofeatures, such as nanotubes. The invention is also directed to a particulate detector incorporating the nanofeature particulate trap. These devices will be collectively referred to as nanotraps herein.

Figure 1:
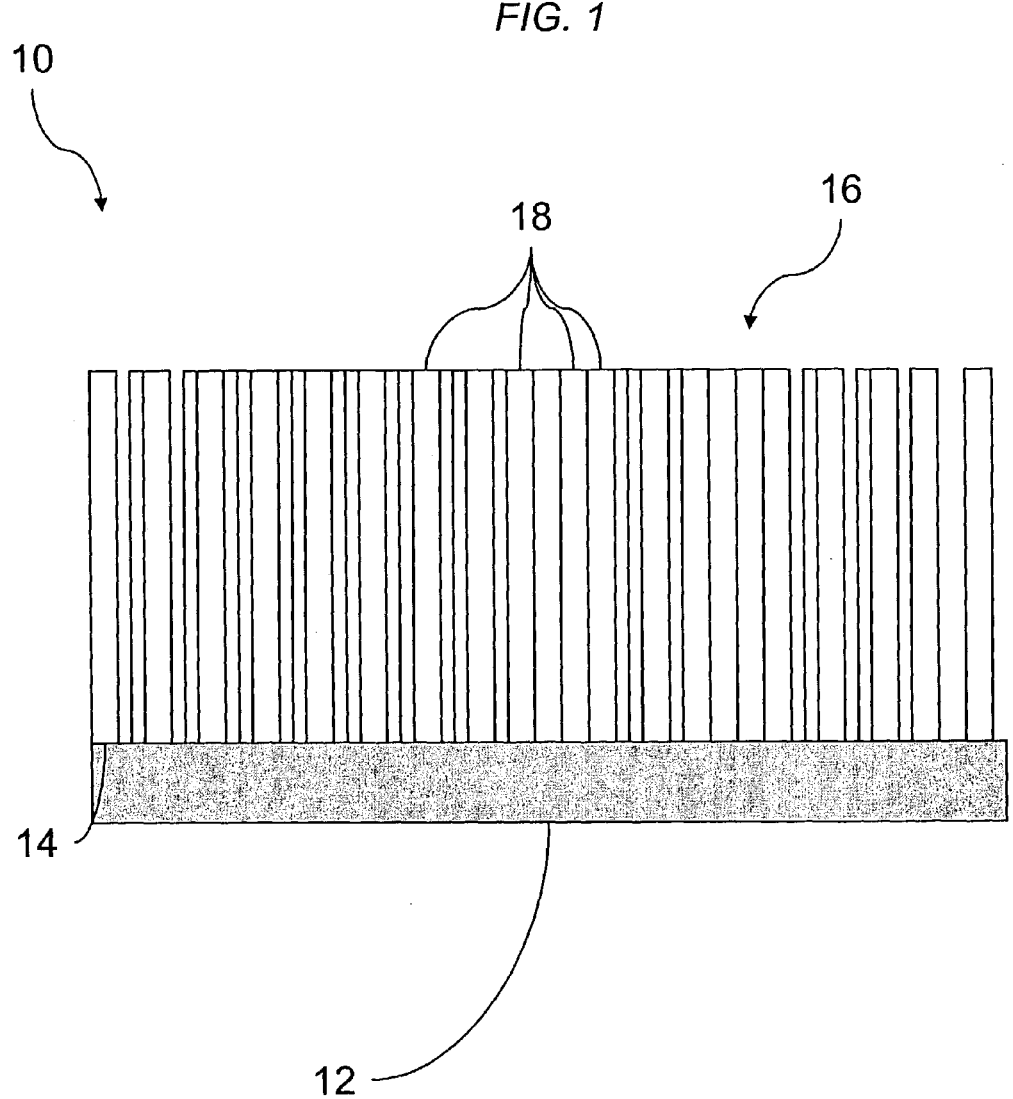
FIG. 1 is a schematic view of an embodiment of a nanotube trap in operation according to the invention.

As shown in FIG. 1, in the most basic embodiment the nanotrap device 10 according to the invention generally comprises a substrate 12, having a growth surface 14 that can additionally be coated with a catalyst to encourage nanofeature growth. A layer 16 of densely packed nanofeatures capable of entrapping particulates of less than 10 microns is then grown on top of the growth surface of the substrate. In the embodiment shown in FIG. 1, the nanofeatures comprise a plurality of nanotubes 18 arranged such that the nanotubes originate and grow normal to the growth surface. Side and top view micrographs of exemplary nanotube nanotraps are shown in FIGS. 2 and 3.

Figure 2:
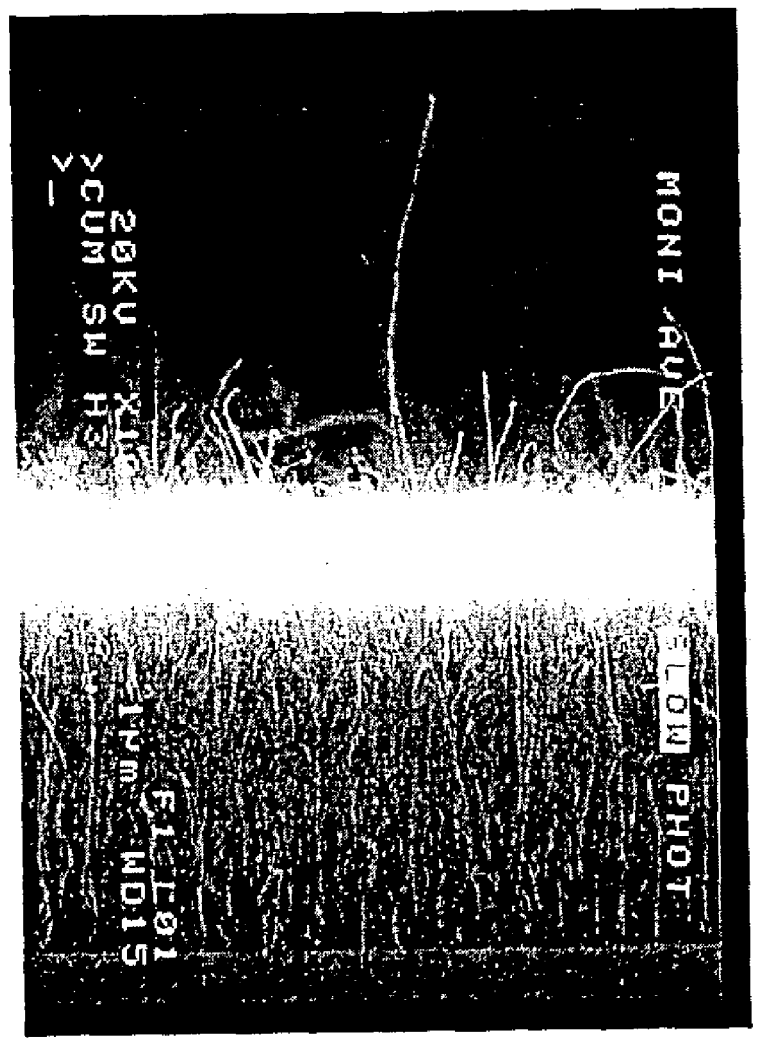
FIG. 2 is a side view micrograph picture of an embodiment of a nanotube trap according to the invention.
Figure 3:
FIG. 3 is a top view micrograph picture of an embodiment of a nanotube trap according to the invention.

Although a nanotube nanofeature is shown in FIGS. 1 to 3, it should be understood that any suitable nanofeature capable of tuned oscillation may be utilized. However, in a preferred embodiment, as shown in FIGS. 1 to 3, and discussed above, a plurality of carbon nanotubes are utilized. Carbon nanotubes possess a combination of properties that make them well suited for use as nanofeatures in a nanotrap. For example, nanotubes combine a nanometer scale diameter with a large aspect ratio, good electrical conductivity, and elastic bending. The small radius of curvature of the nanotubes induces large Van der Walls forces contributing to the "sticking" capabilities of the individual nanotubes. Carbon nanotubes are also hydrophobic facilitating the interaction of bio particulates with the nanotrap in liquid environments. Single-wall nanotubes also have a Young's modulus of approximately 1 TPa, which corresponds to strength/weight ratio approaching 200 times that of steel. The combination of this high Young's modulus and the ability to withstand large strains (~5%) suggests that SWNTs should also have very high breaking strengths.

During operation, the nanotraps shown in FIGS. 1 to 3 utilize the inherently large surface-to-volume ratio of the mats of nanofeatures to promote surface interactions with particulates in the surrounding environment. This is analogous to the operation of the cilia in the lungs, trachea, and nasal epithelia of the human body, which functions similarly as a trap to filter out particulates in the body. Once the particulates come into contact with the nanofeatures of the nanotrap, the above recited properties of the nanofeatures serve to trap the particulates on the nanotrap.

For example, in a liquid environment, the hydrophobic nature of nanotubes could actually function to draw particulates into the nanotrap. Many studies have shown that the range of hydrophobic forces can be on the order of tens to hundreds of nanometers. (Heuberger, et al., *Science*, 292, 905–908 (2001), and Israelachvili, *"Intermolecular and Surface Forces,"Academic Press*, 2nd (1992).) Another inherent property of nanotubes that results in a high trapping efficiency for the inventive nanotraps is the large Van der Waals forces generated by the small size and radius of the features. A similar effect has been observed for the setal tips on the feet of geckos that allow them to adhere to vertical walls. (Autumn et al., *Nature*, 405, 681–685 (2000).)

Alternatively, as discussed, in a nanotrap integrated with a voltage source, the application of relatively small voltages can propogate large electric fields in nanotubes. The electric field thus generated can be used to draw and trap particulates onto the nanotrap through electrostatic interactions.

The combination of these physical factors allows for the efficient trapping of particles ranging from about 0.5 micron to 10 microns. In addition, the growth of nanotubes can be controlled to control the length, diameter and tip curvature or curliness to allow for the possibility of engineering a nanotrap to have particular trapping preference for specifically sized particulates.

Figure 4:
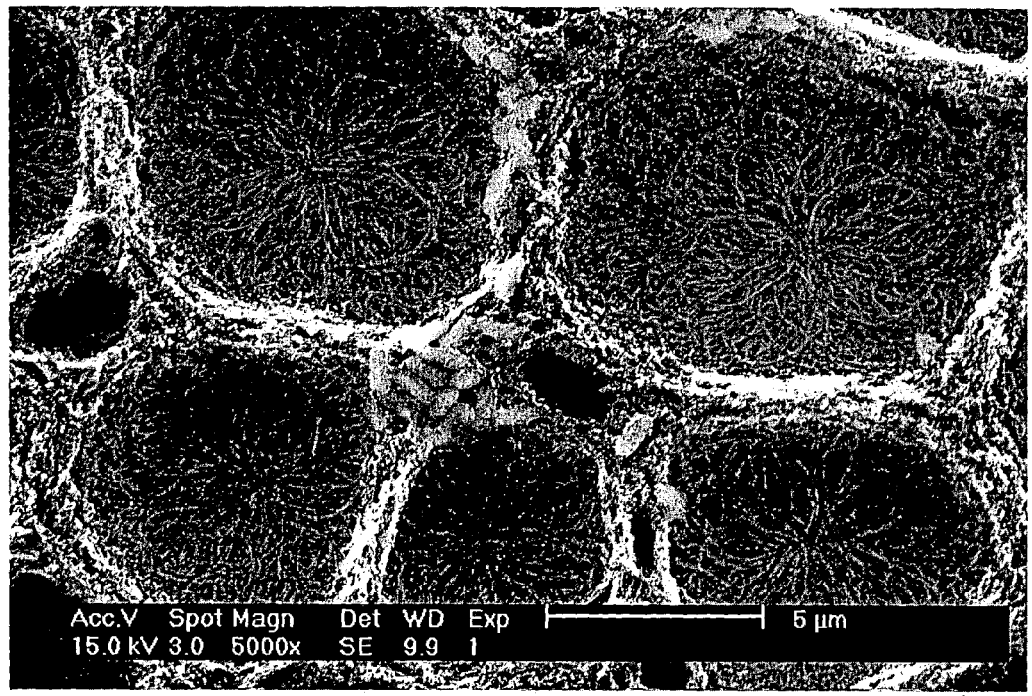
FIG. 4 is a top view micrograph picture of an embodiment of a nanotube trap entrapping *Bacillus pumilus* according to the invention.
Figure 5:
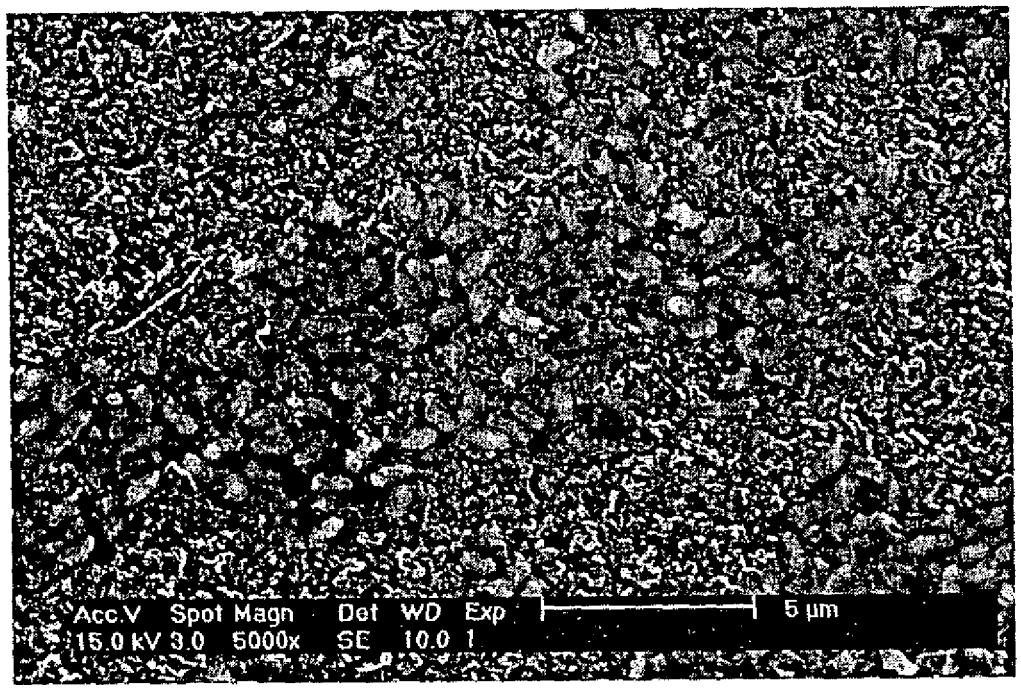
FIG. 5 is a close-up of a top view micrograph picture of an embodiment of a nanotube trap entrapping *Bacillus pumilus* according to the invention.

FIGS. 4 and 5 show the results of an experiment using an exemplary embodiment of the nanotrap according to the current invention having nanotube nanofeatures approximately 10 microns long. The nanotrap was submerged in a solution containing biological spores of *Bacillus pumilis*. As shown, the nanotraps interact with and trap the *Bacillus pumilis* spores onto the surface of the nanotrap.

Although the above discussion has been restricted to a discussion of the construction and operation of the nanotrap, it will be understood that the nanotrap is designed to be incorporated into a detection scheme such that the trapped particulates can be analyzed. In such an embodiment, the detector can be operated in two distinct modes.

In a first mode, the nanotrap having the particulates embedded thereon can be interrogated in-situ by the detector to analyze the trapped particulates. In such an embodiment, any detector capable of interrogating either just the surface of the nanotrap or down to the depth of the nanofeatures (a few microns), such as a laser induced fluorescence or Raman-based techniques. In the later embodiment, all the particulates within a nanotrap could be analyzed at once.

Figure 6:
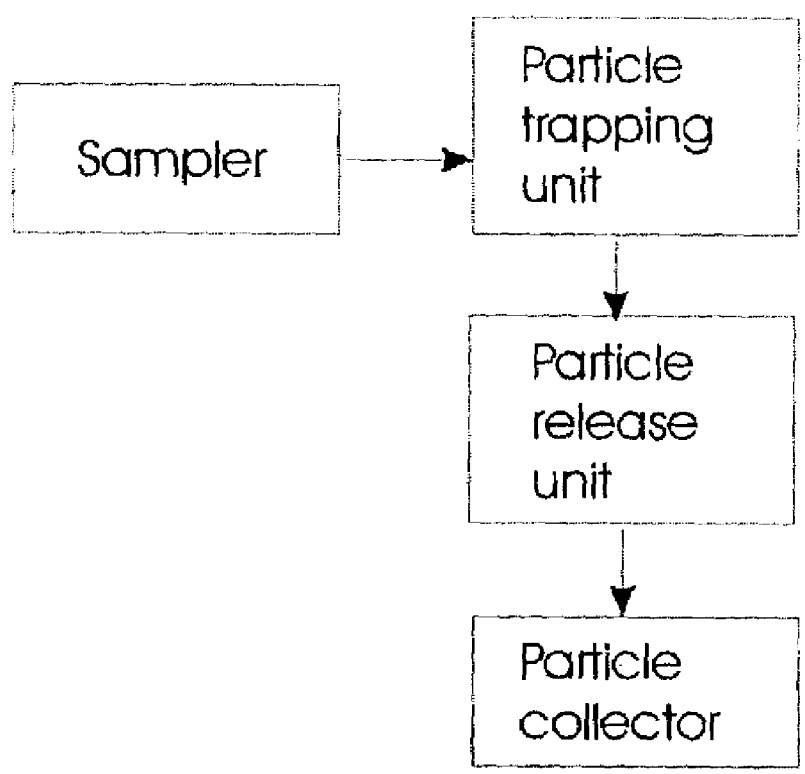
FIG. 6 is a flowchart of an exemplary detection scheme according to the invention.

In a second mode, a flowchart of which is shown in FIG. 6, the particles once trapped are released into the detector through some medium, such as a liquid solution for subsequent analysis. Many potential techniques exist for "releasing" the trapped particulates from the nanotrap in accordance with the current invention. In a first technique the nanotrap can be washed with either a liquid or gas stream to dislodge the particulates, and then this liquid or gas stream can itself be analyzed through any suitable technique. Alternatively, the particles can be dislodged by application of a force to the nanofeatures directly. For example, as discussed above, the application of an electrical field can increase the electrostatic forces between particulates and the nanotrap. By simply reversing the electrical field these attractive electrostatic forces can be used to repulse the particulates into an analyzer. Alternatively, if necessary, the electromechanical resonance properties of nanotubes can be used to "shake" or "cough" the particles off the nanotubes once trapped. This embodiment would, however, require the construction of an actuated or active nanotrap structure.

Although the design and operation of a static nanotrap structure is described above, as discussed the present invention is also directed to an actuated or active nanotrap device 20, which would allow for the active dislodgement of trapped particulates. One exemplary embodiment of such an actuated nanotrap is shown schematically in FIG. 7. In the actuator mode, the nanotubes 22 act as a transducer, converting an input signal 24 into a mechanical action 26, shown in the figures as the dashed nanotubes. In this embodiment, a voltage is applied to the nanotubes to create a charge on the tube and thereby produce a deflection of the individual nanotubes, corresponding to an expansion (which in one embodiment is an elongation) when the tubes are negatively-biased and a contraction when the tubes are positively-biased. This charge induced motion has previously been observed in random arrays of carbon bimorph mats and in graphite sheets, see, e.g., Baughman et al., *Science,* 284 1340 (1999), incorporated herein by reference.

Although not to be bound by theory, it is believed that the nanotube length change is caused by "quantum chemical effects", that is, changes in orbital occupation and band structure result in changes in the C—C bond distances and thus the length of the nanotube. Although the Baughman experiments were done in electrolytic solutions, it should be understood that no electrolytic solution is required so long as direct electrical contact is made with each nanotube. Alternatively, although the charge-induced actuation mechanisms shown in FIG. 7 is only depicted in non-liquid environments, it should be understood that the nanotube electromechanical transduction effect can be compatible with operation in liquids, such as for use in trapping particulates in solution.

Figure 7:
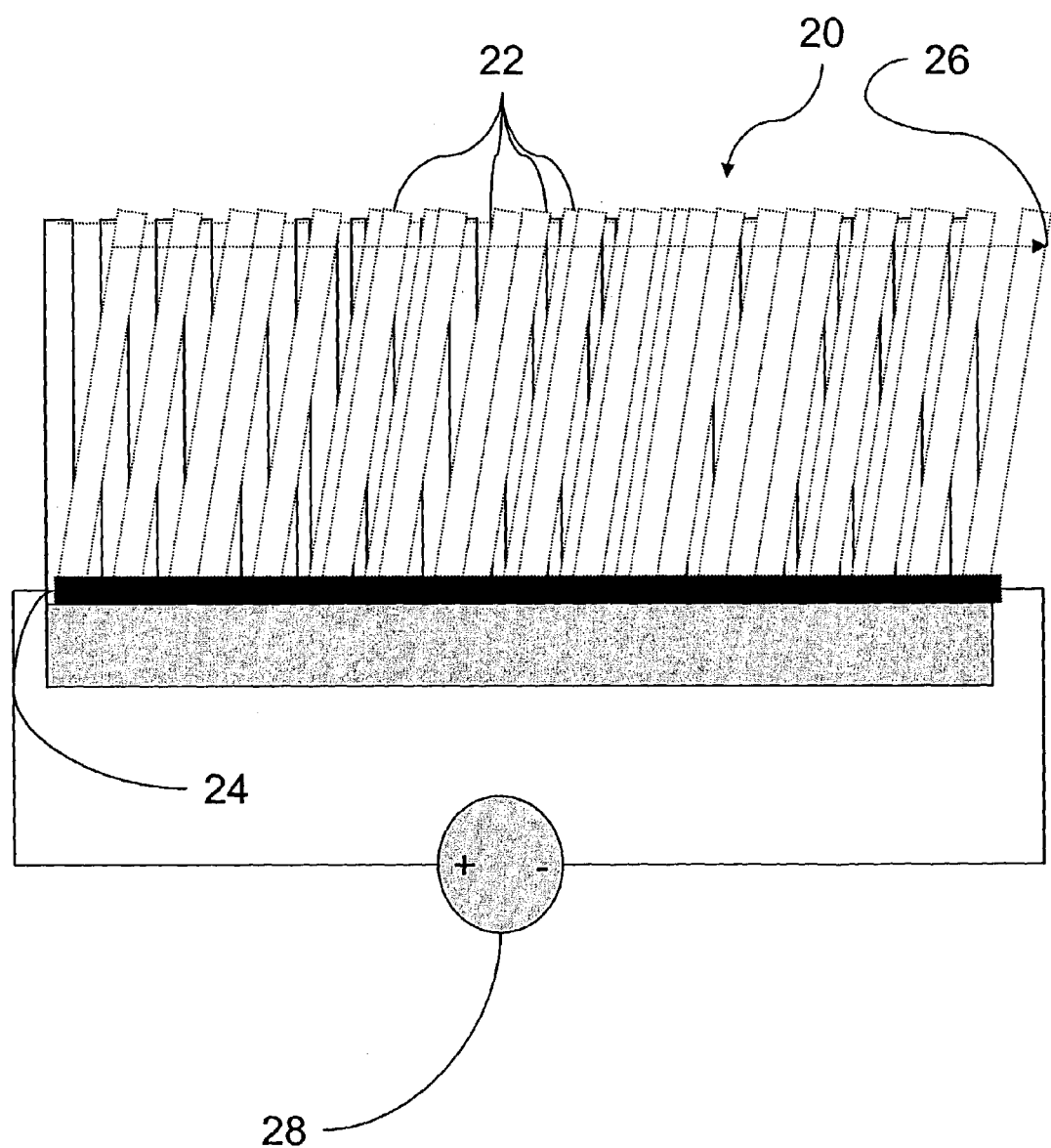
FIG. 7 is a schematic view of an embodiment of an actuated nanotube trap according to the invention.

Regardless of the design, the actuated nanotrap device shown schematically in FIG. 7 functions basically as an oscillator. As shown, in the oscillator mode, each individual nanotube 22 acts as a transducer, converting an input bias 24 into a mechanical oscillation 26. Because range of motion depends on the injected charge, a bias from a tuning control source 28 can be capacitively coupled to the nanotrap such that this bias can be used to control the stress on the rigidly anchored nanotubes 22, thereby allowing for the tuning of the nanotube's mechanical response. An additional RF bias can also be applied to vary the length of the nanotubes at an RF frequency, thereby producing an oscillating deflection of the nanotrap structure.

Figure 8:
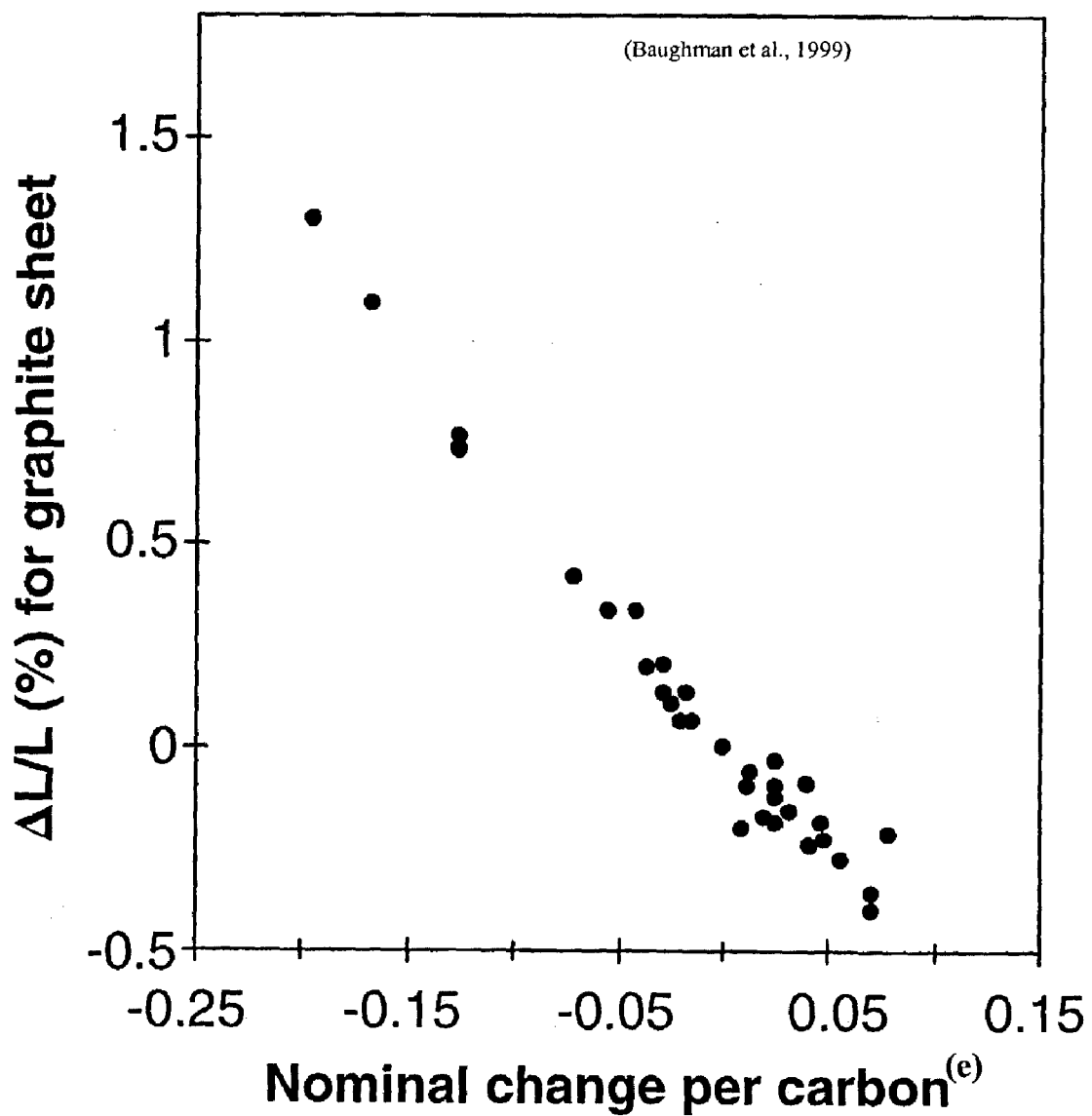
FIG. 8 is a graphical depiction of the electromechanical response of a prior art mat of nanofeatures.

Because the C—C bond length and therefore the overall tube length of the suspended nanotube depends on the injected charge, a capacatively coupled dc bias can be used to control the stress of the suspended tube. The graphite data cited by Baughman et al., as reproduced in FIG. 8 suggests that voltage biases of only a few volts can produce nanotube strains of approximately 1 percent.

Returning to the structure of the underlying nanotrap structure, shown in FIGS. 1 to 3, it should be understood that the substrate can be made of any material which can withstand the temperatures required for growth of the nanofeatures and which can be optionally modified to provide a nucleation area for controllably positioning the nanotrap on a specified area of the substrate for integration with a suitable nanomechanical device. Examples of suitable substrates include metallized Si oxide wafers, alumina, or sapphire.

In turn, any suitable catalyzing metal can be used for the nucleation area on the surface of the substrate, such as, for example, nickel or cobalt. Alternatively, the catalyzing metal could be an alloy of two or more metals such as a Co/Ni or Ti/Ni alloy. The metal catalysts could also be produced by pyrolysis of inorganic or organic metal-containing compounds, such as, for example, Ferric Nitrate or Cobalt Chloride. Although not necessary for the current invention such catalyst regions could be controlled to a limit of sub-50 nm catalyst dots, thus it is possible to nucleate growth of a single nanotube at a catalyst location providing more than adequate control for ensuring proper placement of the nanotrap within a larger nanodetector.

For actuated nanotraps such as that shown in FIG. 7, integrated electrodes can also be produced by combining the catalyst regions with non-catalytic or catalytic electrodes. This ability to precisely locate and orient the growth of the nanotrap and make electrical contact to the nanofeatures provides the basis for fabrication of an actuated nanotrap structure. Such a method may utilize an electron-beam lithography system.

This invention is also directed to a method for growing the dense mats of nanofeatures on a substrate utilizing a chemical vapor deposition (CVD) technique. In one exemplary method, as shown in FIG. 9, the nanotube growth is controlled by pre-patterning growth regions into Si or Si-on-Insulator (SOI) wafers.

The basic technique to construct the alignment structures, such as the static nanotrap shown in FIG. 1, uses a suitable substrate, such as Si or SOI. To ensure proper growth the region upon which the nanofeatures are to grow may be coated with a thin catalyst film such as Ni, Co, or other metal-based mixtures or compounds to nucleate nanofeature growth.

Regardless of the substrated utilized to form the supports and electrodes, a chemical vapor deposition process (CVD) is utilized to grow the nanotubes from the catalyst patterns.

Figure 9:
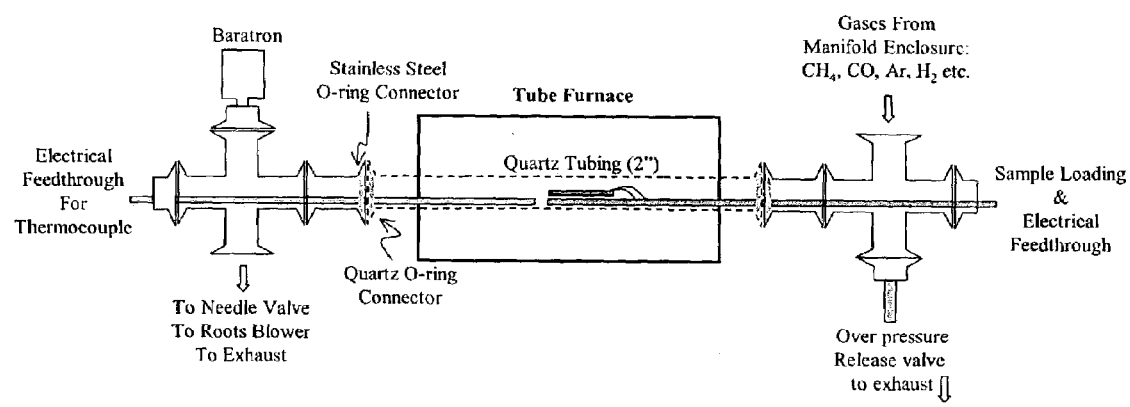
FIG. 9 is a schematic of an apparatus for growing the nanotube trap according to the invention.

In one embodiment, as shown in FIG. 9, a high pressure CVD process uses methane, ethylene, or carbon monoxide in pure form or in a mixture with hydrogen (or ammonia) and argon (or nitrogen) to produce nanotubes on a substrate heated to approximately 500–1000 C.

Further, although one method for the self-assembly of carbon nanotubes is described above, it should be understood that in order to incorporate the carbon nanotube oscillators on CMOS electronics, such as might be necessary when integrating the nanotrap with an analyzer it is necessary to provide carbon nanotube growth at temperatures compatible with processed CMOS circuits, i.e., below about 500° C. Although any suitable method of low temperature growth may be utilized, some exemplary methods include: 1) Murikami et al. (*Appl. Phys. Lett.* 76(13), 1776 (2000)) method for growing carbon nanotube arrays for field emission at <600° C. using bias-enhanced microwave plasma CVD on patterned, nickel-based catalyst at 1–3 Torr; 2) Li et al. (*Appl. Phys. Lett.*, 79(11), 1670 (2001)) method of unaligned nanotube growth on glass at 570° C. using CVD at 100 Torr; 3) low temperature processes for growing carbon nanotubes on silicon (Choi et al., *J. Vac. Sci. Technol. A*, 18(4), 1864 (2000)): using 70 nm nickel films as a catalyst deposited on silicon substrates coated with TiN as an adhesion enhancement layer) and silicon dioxide (Lee et al., *Chem. Phys. Lett.* 327, 277 (2000)) between 500–550° C.; 4) Zhang and Iijima (*Appl. Phys. Lett.*, 75(20), 3087 (1999)) method for growing single-walled carbon nanotubes at 400 C using laser ablation technique with powdered catalyst containing Ni—Co; and 5) Chen et al. (*J. Cryst. Growth*, 193, 342 (1998)) method of growing graphitic nanofibers on nickel substrates at 350–400° C. All of which are incorporated herein by reference.

While the self-assembled nanotraps contemplated in the embodiments discussed so far have been constructed of dense mats of carbon nanotubes made from pyrolyzing an ethylene feedstock over a substrate, the nanofeatures comprising the nanotrap can be of any shape and made by any process and from any material suitable for making self-assembled structures capable of acting in conjunction to trap particulates having dimensions at least as small as 10 micron, such as, for example, spheres or pyramids made of other atomic materials or even biomolecules, such as, for example, proteins. In another embodiment, the nanofeatures may be further functionalized for a variety of applications, such as, for example, being made hydrophilic or hydrophobic, being charged either negatively or positively, or being derivatized with specific chemical groups, etc. In addition, although only an untreated carbon nanotube nanotraps have been shown thus far, in situ sidewall treatments could alter the electrical properties of the nanotubes, such as by increasing the charge differential induced by a given applied voltage.

Finally, although the above discussion has focused on the construction and structure of the nanotrap, it should be understood that a nanomechanical device such as a detector according to the invention may also include a body, a self-contained power supply, and any additional machinery or circuitry necessary for the device's operation. For example, the body of the nanomechanical device itself can be made of any material suitable for micromachining utilizing standard lithographic or MEMS techniques to enclose the nanotrap, such as, for example, aluminum oxide or silicon. In a preferred embodiment, the body further comprises a cap layer, which can be of any design, such that the cap layer protects the nanotrap from unwanted contact with the external environment. Such a cap layer could be made of any suitable material, such as, for example, aluminum oxide or silicon. Such a cap layer could be formed by any conventional MEMS process, such as growth or deposition over a sacrificial layer (not shown) deposited to encapsulate the self-assembled nanotrap wherein the sacrificial layer can subsequently be removed to expose the self-assembled nanotrap itself. Alternatively, these support structures could be formed in a single deposition step with the self-assembled nanotrap. In a more preferred embodiment, one of the substrate, the cap layer, or walls of the nanomechanical device is transparent such that an optical source can be used to interrogate or activate the nanotrap.

In another alternative embodiment, the nanomechanical device may comprise an array of multiple nanotraps such that multiple or parallel processing can be carried out at one time. In this embodiment, the nanotraps can be integrated into a single circuit or detector, such as a laser based particle analyzer. It should be understood that while arrays of nanotraps are discussed above, any suitable alternative geometry of nanotraps may be utilized. Such an embodiment could be used to develop a mobile nanotrap detector device on a chip for mobile detection and analysis of samples. In such an embodiment a portable power source (not shown) would also be integrated into the device.

Further, although the above discussion has been directed to the actual nanotraps and nanotrap analyzer devices according to the present invention, it should be understood that the invention is also directed to suitable nanomechanical devices comprising the nanotraps shown schematically in the above figures.

Although specific embodiments are disclosed herein, it is expected that persons skilled in the art can and will design alternative nanotraps and nanotrap analyzer combinations and methods to produce the nanotrap devices that are within the scope of the following claims either literally or under the Doctrine of Equivalents.

The invention claimed is:

1. A nanotrap comprising:
    a substrate; and
    a plurality of densely packed self-assembled nanofeatures disposed on said substrate, each of said nanofeatures having first and second ends, wherein each of said first ends are independently attached to said substrate, and wherein the nanofeatures are at least 10 microns long such that said second ends are curled and randomly oriented above said substrate to create a collective Van der Waals force capable of attracting and trapping particulates; and
    a voltage source having a controllably oscillating polarity in independent and direct electrical communication with each of said nanofeatures such that application of the oscillating polarity of a voltage from the voltage source to the nanofeatures induces said plurality of nanofeatures to contract and expand to produce an electromechanical actuation of the Plurality of nanofeatures to dislodge any trapped particulates within said nanotrap.

2. The nanotrap described in claim 1 wherein the plurality of nanofeatures are one of either a nanotube or a nanorod.

3. The nanotrap described in claim 1 wherein actuation of the plurality nanofeatures will depend on an additional RF bias applied to the substrate.

4. The nanotrap described in claim 1 wherein the nanotrap is designed to trap particulates having a diameter of 0.5 microns or larger.

5. The nanotrap described in claim 1 wherein the substrate is made of a material selected from the group consisting of silicon, alumina, glass, sapphire or quartz.

6. The nanotrap described in claim 1 further comprising a catalytic material dispersed on said substrate wherein the catalytic material is selected from the group consisting of Fe, Ti, Ni, Co, Mo, Ni/Co alloy, and Ni/Ti alloy.

7. The nanotrap described in claim 1 wherein each of the plurality of nanofeatures has a cross-sectional dimension of about 1 to 100 nm.

8. The nanotrap described in claim 1 wherein the plurality of nanofeatures are of varying lengths.

9. The nanotrap described in claim 1 wherein the plurality of nanofeatures are made of carbon.

10. The nanotrap described in claim 1 wherein the plurality of nanofeatures are grown by self-assembly on the substrate.

11. The nanotrap described in claim 1 wherein the plurality of nanofeatures are chemically or biologically functionalized.

12. The nanotrap described in claim 1 wherein an outer surface of each of the plurality of nanofeatures are treated to increase the resistance of the nanofeatures.

13. The nanotrap described in claim 1, further comprising a device body defining an internal volume wherein the nanotrap is confined within the internal volume.

14. The nanotrap described in claim 13 wherein one of the substrate or device body is transparent.

15. The nanotrap described in claim 13 wherein the device body is made of a material selected from the group consisting of silicon, alumina, glass, sapphire, and quartz.

16. The nanotrap described in claim 1 wherein the device is disposed in a liquid environment.

17. The nanotrap described in claim 1 wherein the device is disposed in a vacuum environment.

18. The nanotrap described in claim 1 wherein the device is disposed in a gaseous environment.

* * * * *